(12) United States Patent
Segina et al.

(10) Patent No.: US 10,286,123 B2
(45) Date of Patent: *May 14, 2019

(54) REMOVABLE BIOCOMPATIBLE SUBSTRATE FILTER FOR A REAMING AND COLLECTION DEVICE

(71) Applicant: Genesis Medical Devices, LLC, Indialantic, FL (US)

(72) Inventors: Daniel Nick Segina, Satellite Beach, FL (US); James Arthur Proctor, Jr., Indialantic, FL (US)

(73) Assignee: Genesis Medical Devices, LLC, Indialantic, FL (US)

( * ) Notice: Subject to any disclaimer, the term of this patent is extended or adjusted under 35 U.S.C. 154(b) by 181 days.

This patent is subject to a terminal disclaimer.

(21) Appl. No.: 15/390,796

(22) Filed: Dec. 27, 2016

(65) Prior Publication Data

US 2017/0112978 A1  Apr. 27, 2017

Related U.S. Application Data

(63) Continuation of application No. 14/305,049, filed on Jun. 16, 2014, now Pat. No. 9,555,169, which is a (Continued)

(51) Int. Cl.
*A61M 1/00* (2006.01)
*A61B 10/02* (2006.01)
(Continued)

(52) U.S. Cl.
CPC ......... *A61M 1/0056* (2013.01); *A61B 10/025* (2013.01); *A61B 17/1635* (2013.01);
(Continued)

(58) Field of Classification Search
CPC .............. A61B 10/025; A61B 10/0283; A61B 17/1635; A61B 2010/0258;
(Continued)

(56) References Cited

U.S. PATENT DOCUMENTS 5,275,609 A * 1/1994 Pingleton ......... A61B 17/32002
600/566
5,354,291 A 10/1994 Bales et al.
(Continued)

OTHER PUBLICATIONS

Synthes Ltd., "Reamer/Irrigator/Aspirator (RIA). For intramedullary reaming and bone Harvesting", <http://www.synthes.com/MediaBin/SUSA/SUBRORIAJ8968b.pdf> Year 2008 (8 Pages).
(Continued)

*Primary Examiner* — Adam Marcetich
(74) *Attorney, Agent, or Firm* — Mark Malek; Daniel Pierron; Widerman Malek, PL

(57) ABSTRACT

The present invention provides for a removable second stage biocompatible substrate filter that includes biocompatible implant material configured to trap second stage operative particulate matter that may include at least one of bone fragments, plasma, stem cells, cellular matter, and growth factors captured from irrigation fluid. The second stage biocompatible substrate filter may be configured to combine with bone fragments captured from irrigation fluid by a first stage filter and may be configured to be operable with a reaming and collection device.

17 Claims, 7 Drawing Sheets

Related U.S. Application Data continuation of application No. 13/091,123, filed on Apr. 21, 2011, now Pat. No. 8,790,321.

(60) Provisional application No. 61/326,234, filed on Apr. 21, 2010.

(51) Int. Cl.
    *A61B 17/16*     (2006.01)
    *A61K 35/28*     (2015.01)
    *A61L 27/36*     (2006.01)
    *A61B 17/00*     (2006.01)

(52) U.S. Cl.
CPC ............ *A61K 35/28* (2013.01); *A61L 27/365* (2013.01); *A61L 27/3608* (2013.01); *A61L 27/3691* (2013.01); *A61M 1/0001* (2013.01); *A61B 10/0283* (2013.01); *A61B 2010/0258* (2013.01); *A61B 2017/00004* (2013.01); *A61B 2017/00969* (2013.01); *A61B 2217/005* (2013.01); *A61B 2217/007* (2013.01); *A61M 2202/005* (2013.01); *A61M 2202/0014* (2013.01); *A61M 2202/0021* (2013.01); *A61M 2202/10* (2013.01); *A61M 2205/7545* (2013.01); *A61M 2210/02* (2013.01)

(58) Field of Classification Search
CPC ........... A61B 2017/00004; A61B 2017/00969; A61B 2217/005; A61B 2217/007; A61K 35/28; A61L 27/3608; A61L 27/365; A61L 27/3691; A61M 1/0001; A61M 1/0056; A61M 2202/0014; A61M 2202/0021

See application file for complete search history.

(56) References Cited

U.S. PATENT DOCUMENTS

| | | | |
|---|---|---|---|
| 5,505,716 A | | 4/1996 | Simmet et al. |
| 5,913,859 A | * | 6/1999 | Shapira ................ A61B 10/025 433/114 |
| 6,013,853 A | | 1/2000 | Athanasiou et al. |
| 6,071,284 A | | 6/2000 | Fox |
| 6,299,763 B1 | | 10/2001 | Ashman |
| 6,325,806 B1 | | 12/2001 | Fox |
| 6,387,070 B1 | | 5/2002 | Marino et al. |
| 6,783,535 B2 | | 8/2004 | Steiner et al. |
| 7,008,394 B2 | | 3/2006 | Geise et al. |
| 7,011,852 B2 | | 3/2006 | Sukavaneshvar et al. |
| 7,351,386 B2 | | 4/2008 | Halstead et al. |
| 7,794,449 B2 | | 9/2010 | Shippert |
| 7,832,566 B2 | | 11/2010 | Leach et al. |
| 8,382,836 B2 | | 2/2013 | Hoerger et al. |
| 8,696,674 B2 | | 4/2014 | Howard et al. |
| 8,790,321 B2 | * | 7/2014 | Segina ................... A61K 35/28 604/319 |
| 9,555,169 B2 | * | 1/2017 | Segina ................... A61K 35/28 |
| 2002/0177785 A1 | * | 11/2002 | Brannon ................ A61B 10/02 600/562 |
| 2003/0161816 A1 | | 8/2003 | Fraser et al. |
| 2005/0025755 A1 | * | 2/2005 | Hedrick ............. A61L 27/3604 424/93.21 |
| 2005/0139532 A1 | | 6/2005 | Hershberger et al. |
| 2006/0106353 A1 | * | 5/2006 | Geneve ................ A61C 1/0076 604/319 |
| 2006/0270974 A1 | | 11/2006 | Goff et al. |
| 2007/0055282 A1 | | 3/2007 | Muschler |
| 2007/0270771 A1 | * | 11/2007 | Ralph ................. A61B 17/1635 604/317 |
| 2007/0276352 A1 | * | 11/2007 | Crocker ............... A61B 10/025 604/500 |
| 2009/0287190 A1 | * | 11/2009 | Shippert ............. A61M 1/0001 604/542 |
| 2009/0306669 A1 | * | 12/2009 | Takahashi ........... A61C 1/0076 606/80 |
| 2010/0055078 A1 | | 3/2010 | Hughes-Mulford |

OTHER PUBLICATIONS

Synthes Ltd., "Reamer/Irrigator/Aspirator (RIA). For intramedullary reaming and bone harvesting." Technique Guide, <www.synthes.com/reprocessing> Jul. 2008, (40 Pages).
USPTO, Non-Final Office Action for U.S. Appl. No. 13/091,123, now U.S. Pat. No. 8,790,321, dated Apr. 3, 2013. (8 Pages).
Applicant, Response to Non-Final Office Action for U.S. Appl. No. 13/091,123, now U.S. Pat. No. 8,790,321, dated Aug. 2, 2013. (19 Pages).
USPTO, Final Office Action for U.S. Appl. No. 13/091,123, now U.S. Pat. No. 8,790,321, dated Oct. 2, 2013. (10 Pages).
Applicant, Response to Final Office Action for U.S. Appl. No. 13/091,123, now U.S. Pat. No. 8,790,321, dated Jan. 2, 2014. (18 Pages).
USPTO, Ex Parte Quayle Office Action for U.S. Appl. No. 13/091,123, now U.S. Pat. No. 8,790,321, dated Jan. 14, 2014. (7 Pages).
Applicant, Response to Ex Parte Quayle for U.S. Appl. No. 13/091,123, now U.S. Pat. No. 8,790,321, dated Feb. 24, 2014. (6 Pages).
USPTO, Notice of Allowance for U.S. Appl. No. 13/091,123, now U.S. Pat. No. 8,790,321, dated Mar. 17, 2014. (5 Pages).
USPTO, Non-Final Office Action for U.S. Appl. No. 14/305,049, dated Nov. 2, 2015. (9 Pages).
Applicant, Response to Restriction Requirement for U.S. Appl. No. 14/305,049, dated Dec. 31, 2015. (10 Pages).
USPTO, Non-Final Office Action for U.S. Appl. No. 14/305,049, dated May 9, 2016. (22 Pages).
Applicant, Response to Non-Final Office Action for U.S. Appl. No. 14/305,049, dated Aug. 8, 2016. (17 Pages).
USPTO, Notice of Allowance for U.S. Appl. No. 14/305,049, dated Sep. 20, 2016. (10 Pages).

* cited by examiner

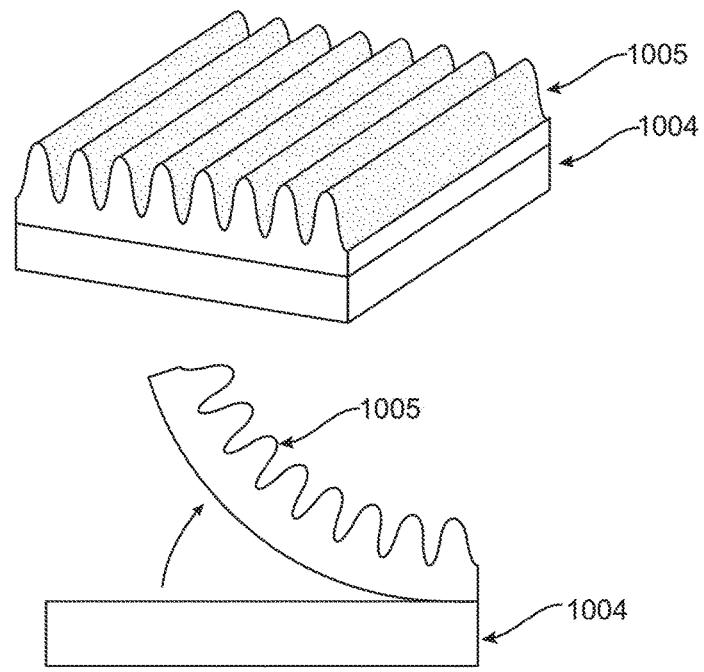
FIG. 11
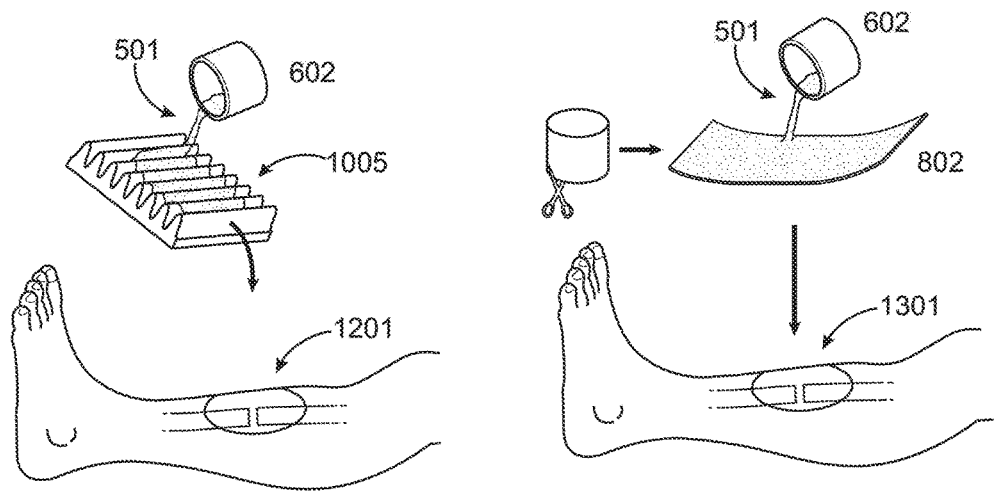
FIG. 12
FIG. 13

REMOVABLE BIOCOMPATIBLE SUBSTRATE FILTER FOR A REAMING AND COLLECTION DEVICE

CROSS REFERENCE TO RELATED APPLICATION

The present application Ser. No. 15/390,796 is a continuation of U.S. patent application Ser. No. 14/305,049 titled Apparatus for Harvesting Improved Bone Graft Material Utilizing an Implantable Biodegradable Filter, filed on Jun. 6, 2014, which, in turn, is a continuation of U.S. patent application Ser. No. 13/091,123 titled Apparatus, System, and Method for Harvesting Improved Bone Graft Material with Reamer-Irrigator-Aspirator (RIA) Device filed on Apr. 21, 2011, which, in turn, claimed priority to U.S. Provisional Patent Application Ser. No. 61/326,234, filed on Apr. 21, 2010, titled Apparatus, System, and Method for Harvesting Improved Bone Graft Material with Reamer-Irrigator-Aspirator (RIA) Device, the entire contents of each of which are hereby incorporated into this application by reference to provide continuity of disclosure.

FIELD OF THE INVENTION

The present invention is in the technical field of medical devices. More particularly, the present invention is in the technical field of harvesting bone graft materials using a reamer device.

BACKGROUND OF THE INVENTION

Currently, materials in the output stream from a reaming device, such as the Reamer-Irrigator-Aspirator provided by Synthes, are not fully and efficiently collected. While there have been some attempts to collect large scale material, other materials such as plasma, and other cellular elements are not currently collected and are discarded. Further, the approach used even to collect the large scale materials, essentially bone fragments, is not efficient for medical personnel to use in the operating room.

SUMMARY OF THE INVENTION

The present invention provides for a removable second stage biocompatible substrate filter that includes biocompatible implant material configured to trap second stage operative particulate matter that may include at least one of bone fragments, plasma, stem cells, cellular matter, and growth factors captured from irrigation fluid. The second stage biocompatible substrate filter may be configured to combine with bone fragments captured from irrigation fluid by a first stage filter, defining a combined product. Furthermore, the second stage filter may be configured to be operable with a reaming and collection device.

The removable second stage biocompatible substrate filter may have a substrate that is a porous and hydrophilic membrane that may be configured as an implantable product for implantation within humans. In this embodiment, the first stage operative particulate matter and the bone fragments may conform to a size and geometric shape consistent with an undulated surface of the second stage filter.

In some embodiments the second stage may be a centrifuge and the combined product may be configured to unroll into sheets.

In some embodiments the bone fragments from the first stage may be a first size and the second stage operative particulate matter may be a second size. Similarly, the second stage biocompatible substrate filter may comprise a biocompatible implant material configured to retain second stage operative particulate matter. The second stage biocompatible substrate filter may be configured to combine with first stage operative particulate matter captured from irrigation fluid by a first stage filter. The first stage operative particulate matter may include material of a first size and the second stage operative particulate matter may include material of a second size.

The removable second stage biocompatible substrate filter may be configured to be operable with a reaming and collection device wherein the second stage operative particulate matter retained may be one of bone fragments, plasma, stem cells, cellular matter, and growth factors captured from irrigation fluid and the first stage operative particulate matter may include bone fragments. Furthermore, the first stage operative particulate matter may include at least one of bone fragments, plasma, stem cells, cellular matter, and growth factors captured from irrigation fluid.

In one embodiment the removable second stage biocompatible substrate filter may include biocompatible implant material configured to retain second stage operative particulate matter wherein the second stage biocompatible substrate filter may be configured to combine with operative particulate matter captured from irrigation fluid by a first stage filter. The first stage retained material and the second stage retained material may be obtained from a reaming device utilizing an irrigation fluid supply and a suction source. An output of the reaming device may be connected to an input of a first stage filter container. In this embodiment, a flow of materials suspended in the irrigation fluid may pass through a first connecting tube and the flow of materials suspended in the irrigation fluid may be filtered by the first stage filter. The first stage retained material may be separated from the flow of materials suspended in the irrigation fluid by a filter possessing a first particulate size selectivity. The first stage filter may further provide a first stage output flow of materials suspended in irrigation fluid. The first stage filter may allow for the collection of a first sized particulate matter of at least one or more of irrigation fluid, plasma, stem cells, growth factors, and cellular matter. Furthermore, the first stage output flow of materials may be suspended in the irrigation fluid and passed through a first stage output. In this embodiment the input of a second stage filter container may be connected by a second connecting tube to the output of the first stage filter container. Therefore, the first stage output flow of materials suspended in the irrigation fluid may be filtered by the second stage filter. In this embodiment the second stage filter may retain a second sized particulate matter different than the first stage filter that includes a portion of at least one or more of plasma, stem cells, growth factors, and cellular matter, and may allow for the passing of a portion of the irrigation fluid as output flow. Additionally, the second stage filter container may include an evacuation port to permit the flow of materials suspended in the irrigation fluid to be evacuated from the second stage filter container in a continuous process. The continuous process may include the first stage filter container receiving output from the reaming device and output from the second stage filter simultaneously. Therefore, the biocompatible substrate may be configured to receive at least a portion of the first stage retained material in combination with at least a portion of the second stage retained material to create a combined graft product.

In this embodiment, the substrate may be a porous and hydrophilic membrane configured as an implantable product for implantation within humans. The first stage retained material and the second stage retained material may conform to a size and geometric shape consistent with an undulated surface of the second stage filter. In some embodiments the second stage may be a centrifuge and the combined product may be configured to unroll into sheets. Furthermore, the first stage may be a grate and the second stage may be a centrifuge or vice versa. As stated above, the substrate may be a porous and hydrophilic membrane of a size and geometric shape consistent with an undulated surface of the second stage filter and configured as an implantable product to envelop a human bone.

BRIEF DESCRIPTION OF THE DRAWINGS

FIG. 11 shows the collagen filter being removed from the stage 2 filter, for use of the retained stage 2 materials.
FIG. 12 shows stage 1 material in one embodiment being added to the stage 2 materials on a collagen filter, pad, or sponge and use as part of a bone graft in a patient. In this case the collagen filter, or sponge would be placed inside the patient along with the stage 1 and stage 2 materials, which may be modified in proportions. The filter, in one embodiment, would dissolve at a later time.
FIG. 13 shows an alternative embodiment of stage 1 materials being added to the stage 2 materials on a collagen filter, pad, or sponge and use as part of a bone graft in a patient.

Note that the specific examples provided are not intended to be limiting but are specific embodiments of the invention. Various alternative materials and processes may be used as known in the art.

DETAILED DESCRIPTION OF THE INVENTION

Figure 1A:
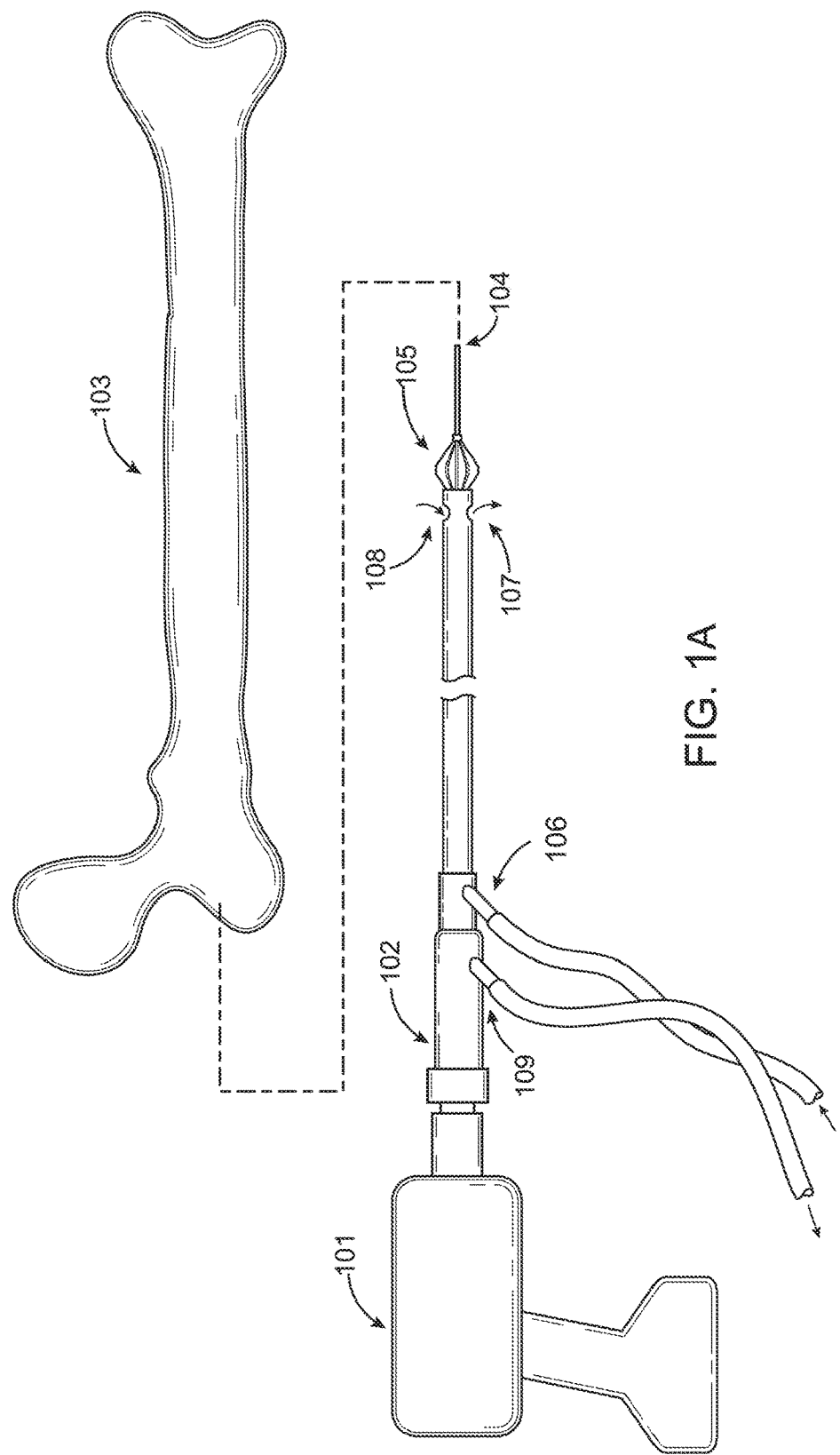
FIG. 1A is a diagram of the prior art RIA device.
Figure 1B:
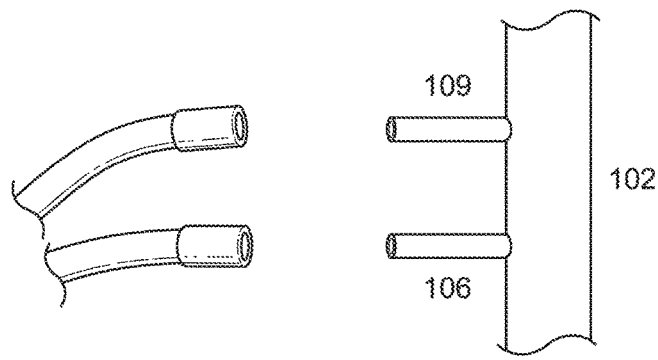
FIG. 1B is a diagram of the prior art RIA device tubing interface.

Referring to FIG. 1A, the depiction of the RIA which stands for Reamer Irrigator Aspirator. Depicted is a power source 101, a drill of any variety used within the operating room. The RIA device 102 which is designed as a medullary bone graft harvesting device. The bone graft material would be harvested from the medullary canal of a native human femur 103 using the RIA device 102. A guide wire 104 is inserted into the medullary canal providing a guide for the RIA device 102 to remain within the medullary canal. The reamer head 105 is designed to cut the bone that is currently being harvested by the device. Through Port 106, the entry portal, saline is pumped into the device exiting out of Port 107. Suction is applied to the device through Port 109, providing an avenue for fluid as well as bone graft material to exit the medullary canal via Port 108. It is then tunneled through Port 109 to a collection device or to the waste suction canister within the operating room. FIG. 1B is a depiction of the current device in larger scale at the region where the suction as well as irrigation ports meet with the RIA device 102. The RIA device 102 with Port 106, is the port allowing for saline to float within the device and Port 109 being the port providing suction and an avenue for the evacuation of material from the medullary canal.

Figure 2:
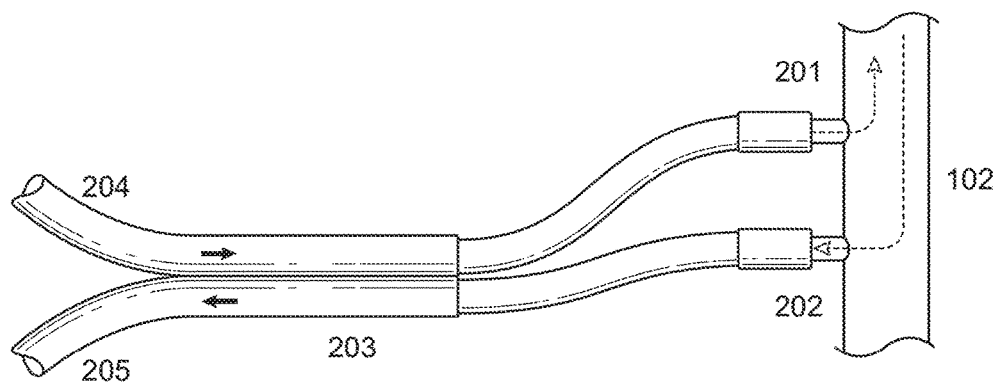
FIG. 2 shows the bi-lumen tube conned to a tube port in a RIA or other device.

FIG. 2 is a depiction of the improved tubing system in one embodiment of this current invention. Depicted is the RIA device 102 with modified coupling Zones 201 as well as 202. 201 would be the coupling point for saline inflow into the RIA device 102; whereas, Port 202 would provide for efflux and evacuation of fluid as well as bone graft material that is applied via suction. The suction source would be obtained through a source available within the operating room. The tubing is coupled 203 to provide for less entanglement and more streamlined use within the operating room. These tubes would branch allowing for filtration/separation canisters, to be described later. Tube 204 would provide an inflow source for saline whereas Tube 205 would provide suction as well as an egress pathway for bone graft as well as saline or other fluids.

Figure 3:
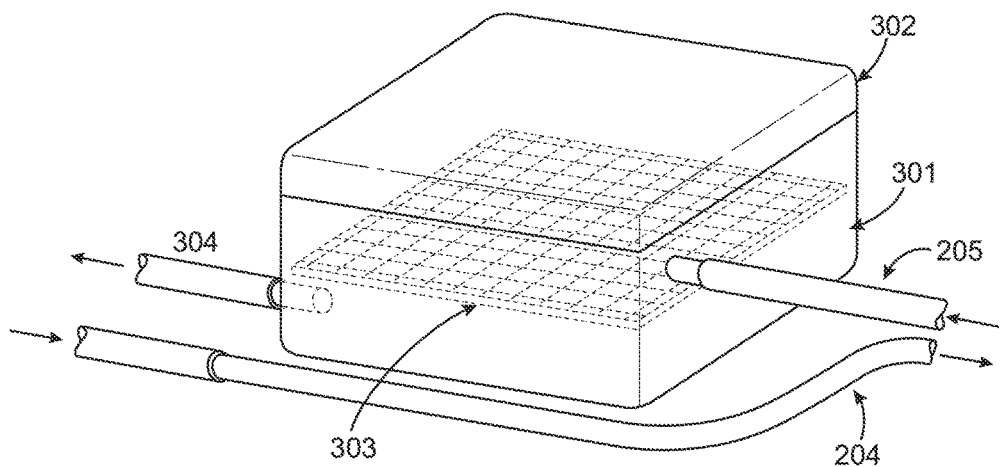
FIG. 3 shows the improved stage 1 filter with the water irrigation hose bypassing the filter (not integrated).

FIG. 3 depicts an embodiment of a modified Stage 1 filter for the collection of materials from the harvesting site. Saline and bone graft material would flow into the device via Tube 205. The device container, 301, would contain a hinged lid 302. Within the container 301, would be a Removable Porous Filter, 303, that is porous in nature to capture large bone graft material but provide for the flow through of saline, blood products, plasma, cells, and growth factors, and other particulate matter of a specific geometrically limited size. The material would be drawn through the filter via suction applied through Tube 304. Also depicted in FIG. 3 would be Tubing 204 that would allow for saline to flow to the RIA device 102 and provide irrigation to facilitate the evacuation of bone graft material.

Figure 4:
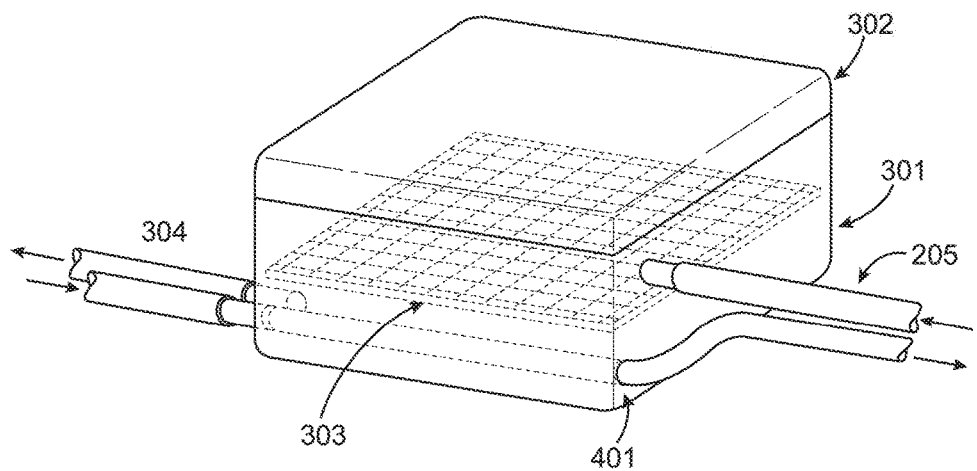
FIG. 4 shows the Stage 1 filter with an integrated pass through irrigation source hose for use with the bi-lumen tubing.

FIG. 4 is an alternative embodiment of the Stage 1 filter. Tube 401 would be contained within the Filter Device container, 301, once again avoiding significant entanglement and providing for more efficient use within the operating room. The remaining portion of the device would function very similar as the device in FIG. 3. A hinged lid, 302, providing access to Porous Filter 303, would catch material entering via Tube 205 once again allowing for saline, blood products, plasma, cells, growth factors and other particulate matter of a specific geometrically limited size to pass through and be drawn out via Port 304.

Figure 5:
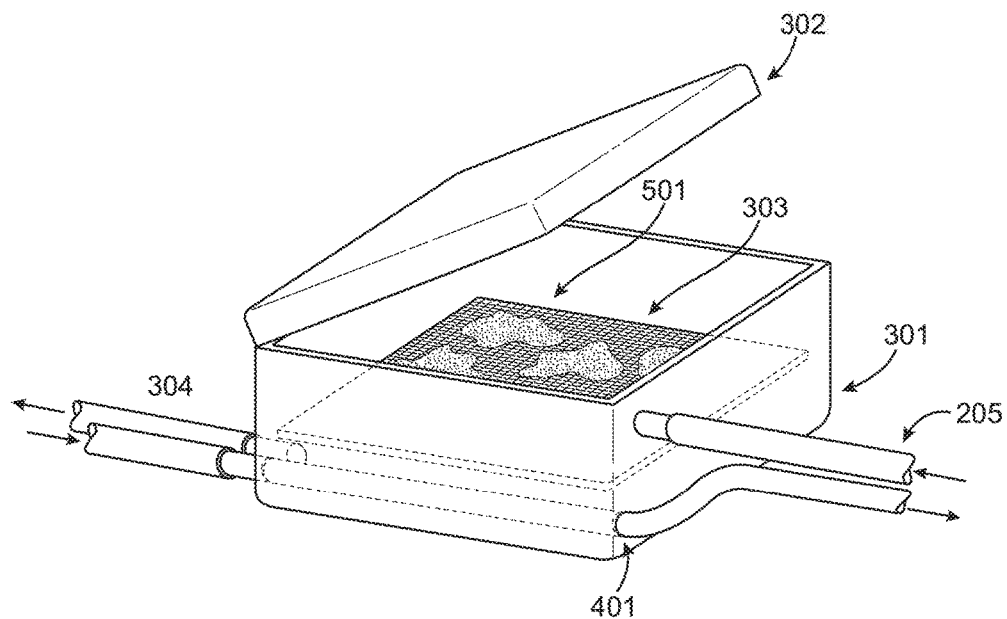
FIG. 5 shows the stage 1 filter with the lid open, and stage 1 material inside.

FIG. 5 shows one depiction of the initial stage filter with additional details noted. Through Tube 205 saline as well as graft material evacuated from the medullary canal would enter Stage 1 container 301. The lid now hinged open, depicted at 302, allows for access to Porous Filter 303 containing Bone Graft Material 501. The remaining portion of the fluid, containing blood products, plasma, cells, growth factors and other particulate matter of a specific geometrically limited size would be evacuated via suction, through Tube 304.

Figure 6:
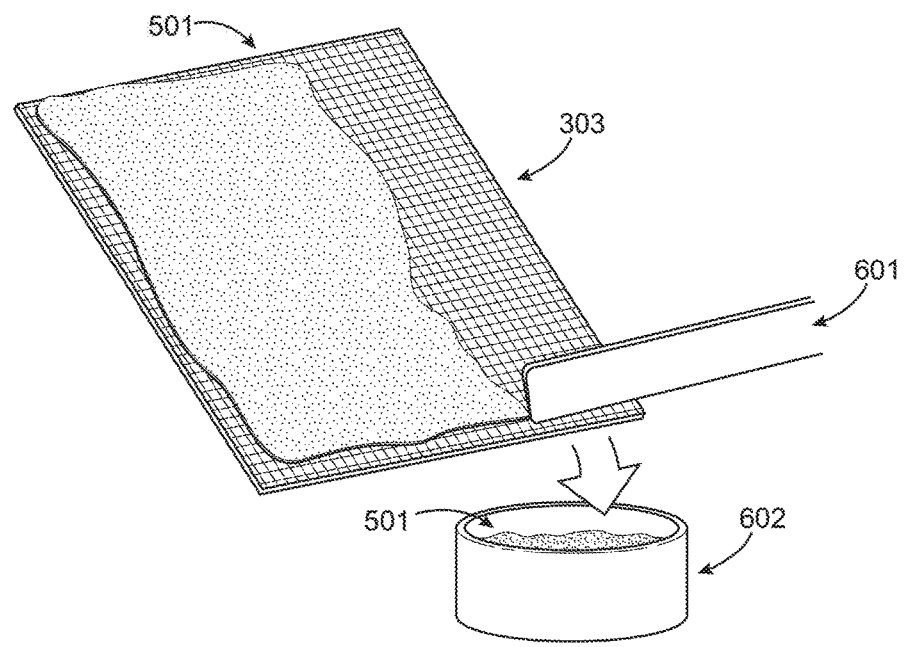
FIG. 6 shows the removed filter plate from the stage 1 filter with the stage 1 material being collected from the filter plate into a canister for later use.

FIG. 6 depicts the removal of the material off of Porous Filter 303. Bone Graft Material 501 would then be removed via Spatula Device 601 into Container 602. These Devices, 601 as well as 602, would be sterile and used within the operative field. The Collection Container 602 provides for a sterile container to contain the Bone Graft Material 501 for later re-implantation at the desired clinical site.

Figure 7:
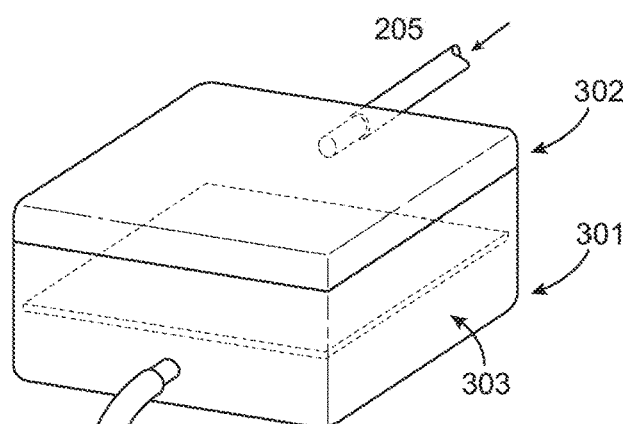
FIG. 7 shows the stage 1 filter connected to a stage 2 collector centrifuge, with a collagen sponge or filter cylinder inside in one embodiment of the invention.

FIG. 7 represents one embodiment of the second stage filtration system which would be designed to remove excess water yet retain additional graft material including but not limited to blood products, plasma, cellular bone marrow/stem cell elements, as well as growth factors and other particulate matter of a specific geometrically limited size. Depicted in FIG. 7 is the Porous Filter 303 contained within the Filtration container 301 covered by Lid 302. Initial material harvested from the RIA device 102 would enter the container via Tube 205. Large bone graft material would be trapped by Porous Filter 303 allowing for the pass through/flow through of the remaining material through Tube 304. This material once again would represent blood products, plasma, and cellular elements including stem cells as well as growth factors and other particulate matter of a specific geometrically limited size. This material would then enter Centrifugal Filtration Device 701. This device would contain a porous filtration capturing membrane 801. It will be covered and contained within the centrifugal filtration device via Lid 703. The porous filtration capturing membrane 801 would be porous in its design to allow for capturing of blood products, plasma, cellular elements/stem cells, as well as growth factors and other particulate matter of a specific geometrically limited size, yet provide for the separation of fluid. This separation would then allow for a concentration of the graft elements and further to extract fluid from the system via centrifugation. The fluid may exit via Tubing 702 connected to an evacuation port in the various embodiments of the second stage filter as illustrated, for example, in FIG. 7.

Figure 8:
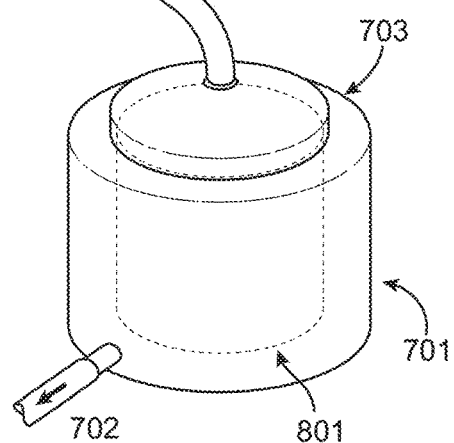
FIG. 8 shows the collagen filter removed from the centrifuge after collection, then cut into a flat "pad" of stage 2 material on the collagen filter or sponge in one embodiment.
Figure 8:
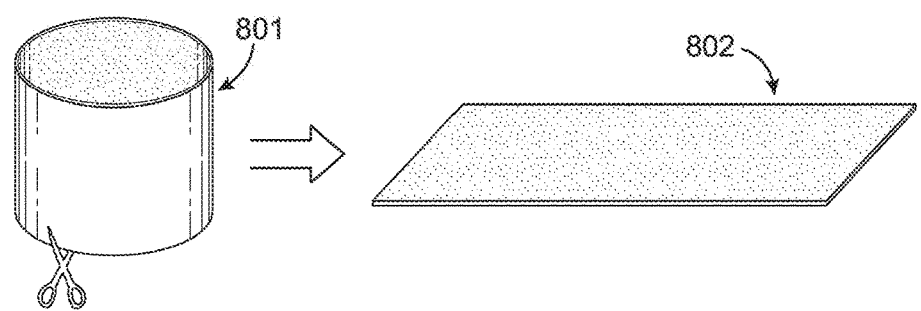

FIG. 8 is a detailed depiction of the porous filtration capturing membrane within the Filtration Device 701. The cylindrical porous filtration capturing membrane 801 would be removed from Centrifugal Filtration Device 701 and cut to provide for a rectangular surface and function as a graft impregnated membrane for re-implantation within the patient.

Figure 9:
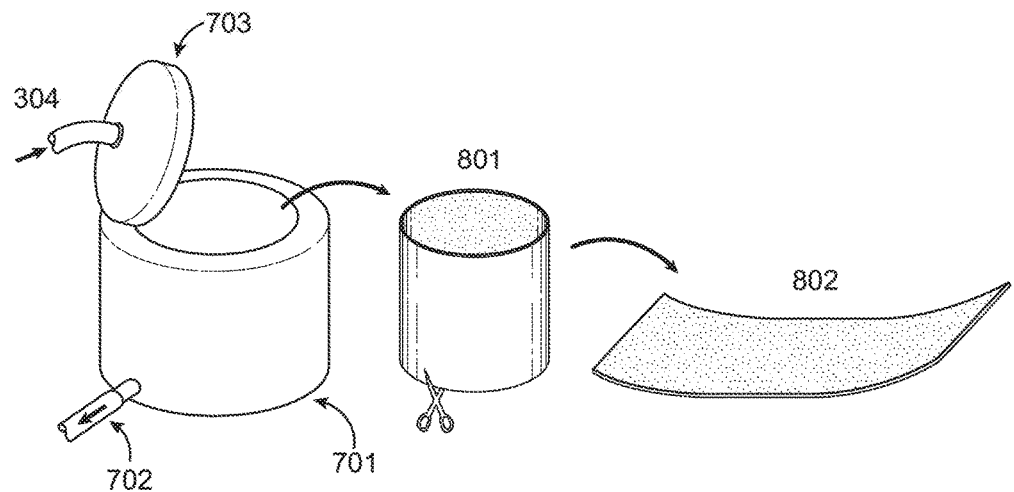
FIG. 9 shows the collagen or other filter material removed from the centrifuge, cut and laid flat as a stage 2 pad.

FIG. 9, once again, provides for a drawing of this process starting with the Centrifugal Filtration Device 701 that is sealed via Lid 703. Material filtered through the first stage filtration system enters via Tube 304. After a centrifugal filtration process takes place, within 701, the material is trapped within the porous filtration capturing membrane 801 which is porous in nature to provide for the capture of blood products, plasma, cellular elements including stem cells, as well as growth factors and other particulate matter of a specific geometrically limited size, but allow for the pass through of fluid that would exit via Tubing 702 connected to an evacuation port in the various embodiments of the second stage filter as illustrated, for example, in FIG. 9. The porous filtration capturing membrane 801 could then be cut to size and later implanted within the patient.

Figure 10:
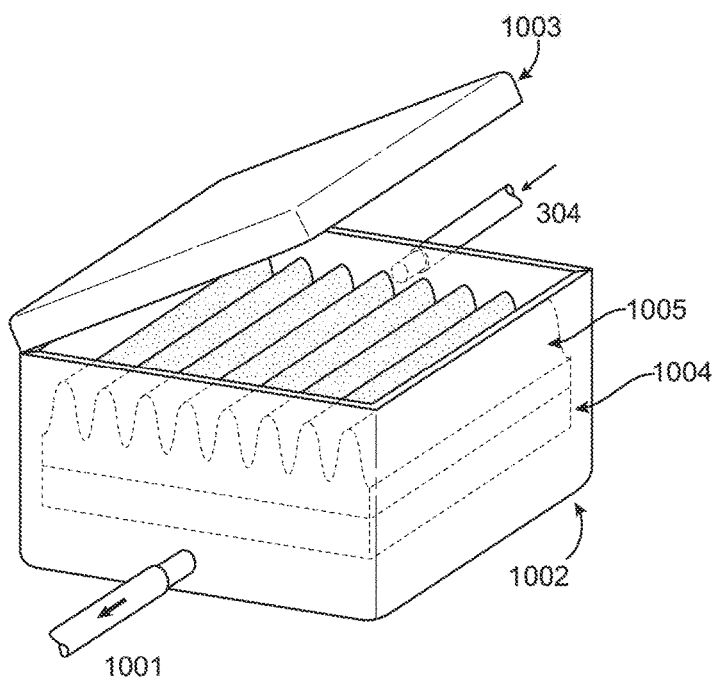
FIG. 10 shows an alternative stage 2 collector using a filtration system, containing a collagen or other materials filter plate or sponge.

FIG. 10 represents an alternative embodiment of the second stage filter. This filter would be designed for a more passive filtration process facilitated by vacuum negative pressure. Filtration Canister 1002 would contain a Hinged Lid 1003. Material exiting the first stage filter would enter the device via Tube 304. The undulating surface depicted as 1005 would be a filtration surface undulated for increasing surface area. It would reside on top of a porous yet Hydrophilic Membrane 1004 that would facilitate the extraction of fluid. The retention of blood products, plasma, cellular elements including stem cells, growth factors and other particulate matter of a specific geometrically limited size, would take place on the second stage (or any subsequent stage) filtration surface 1005. Excess fluid would then be evacuated via Tube 1001 connected to an evacuation port in the various embodiments of the second stage filter as illustrated, for example, in FIG. 10.

In FIG. 11 a more detailed depiction of the second stage filter and hydrophilic membrane is depicted. The undulating Second Stage Filter 1005 would initially lie on top of porous Hydrophilic Membrane 1004. The Filtration Surface 1005 would then be peeled away from hydrophilic/porous Surface 1004 after it has been exposed to the second stage graft/fluid material. This surface would then be available for implantation within the desired clinical setting.

FIG. 12 represents the final combination of material from the first as well as second stage of filtration, or any combination of a plurality of filtration stages. Material from the first stage of filtration, depicted as 501, and being contained within Sterile Container 602, would then be placed on top of Undulating Porous Sponge 1005. This would become a combination graft of large fragments of bone graft material from stage 1 combined with desired blood products, plasma, cellular elements/stem cells, growth factors and other particulate matter of a specific geometrically limited size. This combined graft can then be used in the desired clinical location. The location being depicted in FIG. 12 as 1201, a tibial bone graft site, although other site may be desired.

An alternative embodiment of the combined graft would be depicted in FIG. 13 that would provide for a combination of material from the first stage filtration as well as material captured via centrifugal filtration device and contained within the porous filtration capturing membrane 801. Material 501 from the first stage of Filtration would be removed from Container 602. It would then be placed on the cut porous filtration capturing membrane 801, which would contain blood products, plasma, cellular elements including stem cells as well as growth factors and other particulate matter of a specific geometrically limited size. This would then be made available for implantation within a desired clinical bone graft site depicted as a tibial site 1301 in FIG. 13, although other site may be desired.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

That which is claimed is:

1. A removable second stage biocompatible substrate filter comprising:
   biocompatible implant material configured to trap second stage operative particulate matter;
   wherein the second stage operative particulate matter includes at least one of bone fragments, plasma, stem cells, cellular matter, and growth factors captured from irrigation fluid;
   wherein the removable second stage biocompatible substrate filter is configured to combine with bone fragments captured from irrigation fluid by a first stage filter, defining a combined product;
   wherein the removable second stage biocompatible substrate filter is configured to be operable with a reaming and collection device; and
   wherein the second stage biocompatible substrate filter is configured to be removable from a filter device container.

2. The removable second stage biocompatible substrate filter of claim 1 wherein the removable second stage biocompatible substrate filter is a porous and hydrophilic membrane configured as an implantable product for implantation within humans.

3. The removable second stage biocompatible substrate filter of claim 2 wherein the removable second stage biocompatible substrate filter is configured as an implantable product; and wherein the first stage operative particulate matter and the bone fragments conform to a size and geometric shape consistent with an undulated surface of the second stage filter.

4. The removable second stage biocompatible substrate filter of claim 1 wherein the second stage is a centrifuge.

5. The removable second stage biocompatible substrate filter of claim 1 wherein the combined product is configured to unroll into sheets.

6. The removable second stage biocompatible substrate filter of claim 1 wherein the bone fragments from the first stage are a first size; and wherein the bone fragments from the second stage operative particulate matter is a second size.

7. A removable second stage biocompatible substrate filter comprising:
   biocompatible implant material configured to retain second stage operative particulate matter;
   wherein the removable second stage biocompatible substrate filter is configured to combine with first stage operative particulate matter captured from irrigation fluid by a first stage filter;
   wherein the first stage operative particulate matter includes material of a first size; and
   wherein the second stage operative particulate matter includes material of a second size; and
   wherein the second stage biocompatible substrate filter is configured to be removable from a filter device container.

8. The removable second stage biocompatible substrate filter of claim 7 wherein the removable second stage biocompatible substrate filter is configured to be operable with a reaming and collection device.

9. The removable second stage biocompatible substrate filter of claim 7 wherein the second stage operative particulate matter retained is one of bone fragments, plasma, stem cells, cellular matter, and growth factors captured from irrigation fluid.

10. The removable second stage biocompatible substrate filter of claim 7 wherein the removable second stage biocompatible substrate filter is configured to receive first stage operative particulate matter that includes bone fragments.

11. The removable second stage biocompatible substrate filter of claim 7 wherein the removable second stage biocompatible substrate filter is configured to receive first stage operative particulate matter that includes at least one of bone fragments, plasma, stem cells, cellular matter, and growth factors captured from irrigation fluid.

12. A removable second stage biocompatible substrate filter comprising:
   biocompatible implant material configured to retain second stage operative particulate matter;
   wherein the removable second stage biocompatible substrate filter is configured to combine with operative particulate matter captured from irrigation fluid by a first stage filter;
   wherein the first stage retained material and the second stage retained material are obtained from a reaming device utilizing an irrigation fluid supply and a suction source;
   wherein an output of the reaming device is connected to an input of a first stage filter container;
   wherein a flow of materials suspended in the irrigation fluid passes through a first connecting tube;
   wherein the flow of materials suspended in the irrigation fluid is filtered by the first stage filter;
   wherein the first stage retained material is separated from the flow of materials suspended in the irrigation fluid by a filter possessing a first particulate size selectivity that provides a first stage output flow of materials suspended in irrigation fluid;
   wherein the first stage filter allows for collection of a first sized particulate matter of at least one or more of irrigation fluid, plasma, stem cells, growth factors, and cellular matter;
   wherein the first stage output flow of materials is suspended in the irrigation fluid and passed through a first stage output;
   wherein an input of a second stage filter container is connected by a second connecting tube to the output of the first stage filter container;
   wherein the first stage output flow of materials suspended in the irrigation fluid is filtered by the second stage filter;
   wherein the second stage filter retains a second sized particulate matter different than the first stage filter;
   wherein the second stage filter collects a portion of at least one or more of plasma, stem cells, growth factors, and cellular matter, and allows for passing of a portion of the irrigation fluid, as output flow;
   wherein the second stage filter container includes an evacuation port to permit the flow of materials suspended in the irrigation fluid to be evacuated from the second stage filter container in a continuous process;
   wherein the second stage biocompatible substrate filter is configured to receive at least a portion of the first stage retained material in combination with at least a portion of the second stage retained material to create a combined graft product; and
   wherein the second stage biocompatible substrate filter is configured to be removable from a filter device container.

13. The removable second stage biocompatible substrate filter of claim 12 wherein the substrate is a porous and hydrophilic membrane configured as an implantable product for implantation within humans.

14. The removable second stage biocompatible substrate filter of claim 12 wherein the removable second stage biocompatible substrate filter is configured as an implantable product; and wherein the first stage retained material and the second stage retained material conform to a size and geometric shape consistent with an undulated surface of the second stage filter.

15. The removable second stage biocompatible substrate filter of claim 12 wherein the second stage is a centrifuge.

16. The removable second stage biocompatible substrate filter of claim 12 wherein the combined product is configured to unroll into sheets.

17. The removable second stage biocompatible substrate filter of claim 12 wherein the substrate is a porous and hydrophilic membrane of a size and geometric shape consistent with an undulated surface of the second stage filter configured as an implantable product to envelop a human bone.

* * * * *